United States Patent [19]
Levine

[11] Patent Number: 5,638,841
[45] Date of Patent: *Jun. 17, 1997

[54] DEVICE AND METHOD FOR DENTAL FLOSSING

[76] Inventor: Steven K. Levine, 34 Cross Ridge Rd., Chappaqua, N.Y. 10514

[ * ] Notice: The term of this patent shall not extend beyond the expiration date of Pat. No. 5,406,965.

[21] Appl. No.: 423,054

[22] Filed: Apr. 17, 1995

Related U.S. Application Data

[63] Continuation-in-part of Ser. No. 93,419, Jul. 19, 1993, Pat. No. 5,406,965.
[51] Int. Cl.$^6$ ............................................. A61C 15/00
[52] U.S. Cl. .......................................................... 132/323
[58] Field of Search ................................. 132/323, 324, 132/325, 326, 327

[56] References Cited

U.S. PATENT DOCUMENTS

| | | |
|---|---|---|
| D. 265,515 | 7/1982 | Levine . |
| D. 272,565 | 2/1984 | Levine . |
| D. 276,378 | 11/1984 | Levine . |
| D. 322,491 | 12/1991 | Huskey . |
| 1,091,789 | 3/1914 | Andren . |
| 1,217,264 | 2/1917 | Baxter . |
| 2,467,221 | 4/1949 | Pastl . |
| 2,648,341 | 8/1953 | Moll . |
| 2,664,093 | 12/1953 | Carpenter . |
| 2,784,772 | 3/1957 | Chamberlin et al. . |
| 2,837,098 | 6/1958 | Sorboro . |
| 3,393,687 | 7/1968 | Whitman . |
| 3,472,247 | 10/1969 | Borsum et al. . |
| 3,631,869 | 1/1972 | Espinosa . |
| 3,718,146 | 2/1973 | Myers . |
| 3,734,107 | 5/1973 | Thierman . |
| 3,799,177 | 3/1974 | Bragg . |
| 3,834,404 | 9/1974 | Chien . |
| 3,939,853 | 2/1976 | Spanondis . |

FOREIGN PATENT DOCUMENTS

2 122 495   1/1984   United Kingdom .

*Primary Examiner*—Nicholas D. Lucchesi
*Attorney, Agent, or Firm*—Stroock & Stroock & Lavan

[57] ABSTRACT

The present invention relates to an improved device and method for flossing teeth. The device has a handle portion and a finger portion. The finger portion is inserted into an individual's mouth, and the handle portion is used for holding the dental flossing device. In a first embodiment, the dental flossing device has two apertures spaced along the finger portion. The flossing material is threaded through the first aperture and then the second aperture. The user can also wrap the floss around the finger portion of the stick member to increase the friction between the floss and the stick member to facilitate flossing. A user presses one end of the flossing material against the device to keep the flossing material taut. The other end of the flossing material, extending from an aperture at the distal end of the device, is held by the user's fingers or is wrapped around a finger, depending on the individual's personal technique. Thereafter, the finger portion of the device is inserted into the mouth and flossing is performed. In a second embodiment, the device has only a single aperture through which the floss is threaded, a section of the floss being held against a side of the device by the hand of the user during use.

34 Claims, 4 Drawing Sheets

DEVICE AND METHOD FOR DENTAL FLOSSING

REFERENCE TO RELATED APPLICATION

This is a continuation-in-part application of U.S. patent application Ser. No. 08/093,419, filed on Jul. 19, 1993 now U.S. Pat. No. 5,406,965.

BACKGROUND OF THE INVENTION

The present invention relates generally to a device for flossing teeth and, in particular, a device for improving the ability of a person to extract food and other particles from between teeth and to aid in the prevention of infections, diseases, tooth decay and other problems associated with poor dental hygiene.

In the past, devices for flossing one's teeth have been very complicated, having handles which contain a spool of dental floss therein, the floss being fed through a shaft and pulled off the spool through an aperture at the tip of the shaft. Such inventions are disclosed in U.S. Pat. No. 3,734,107, U.S. Pat. No. 4,434,807 and U.S. Pat. No. Design 322,491. However, these types of dental flossing devices have numerous drawbacks. Specifically, dental floss must be purchased which is adapted for the specific dental flossing device being used. Furthermore, these devices can be relatively expensive as well as relatively bulky, and therefore difficult to carry for use when needed, such as after meals.

Other dental flossing devices comprise fork-like prongs separated a distance sufficient to contain therebetween a section of dental floss. However, one problem with these devices is the inability to obtain the necessary range of movement within one's mouth. Furthermore, a user may have trouble reaching deep within the back of the mouth with these devices. Another defect in such devices is the need to remove such devices from the mouth and reset a new length of floss when a change in floss is desired or the floss breaks. A representative selection of these devices can be seen in U.S. Pat. Nos. 3,939,853; 3,799,177; 3,472,247; 3,734,107; 3,834,404; 2,837,098; 2,784,722; 2,467,221; 1,217,264 and 1,091,789.

Flossing tools have also been formed of a single member but including means for securing one end of the floss to the tool by means of a knot, or a knob about which the floss can be wrapped. Examples of such devices include U.S. Pat. No. 3,393,687; U.S. Pat. No. 1,890,788; U.S. Pat. No. Design 272,565; U.S. Pat. No. Design 265,515 and U.S. Pat. No. Design 276,378. However, those devices have the drawbacks of requiring removal from the mouth and manipulation to advance a fresh length of floss. This increases the time required for flossing and complicates use.

Still another variation on flossing tools also involves the use of a single device bent at its end to provide two points for securing a length of floss therebetween. Examples of these tools include U.S. Pat. No. 2,664,093 and U.S. Pat. No. 2,648,341.

Accordingly, it is desired to provide an improved flossing device for flossing one's teeth having a construction which will allow a user to more efficiently floss, as well as providing the easiest transition from using only one's fingers to using the present invention, regardless of an individual's personal flossing techniques.

SUMMARY OF THE INVENTION

Generally speaking, in accordance with the present invention, an improved dental flossing device is provided including an elongated stick member having a handle portion and a finger portion, the handle portion having a first end and a second end and the finger portion having a near end and a free end, with the near end of the finger portion connected to the second end of the handle portion. The stick member has a first aperture for receiving a length of dental floss, the aperture positioned essentially near the connection of the near end of the finger portion and the second end of the handle portion. The stick member also has a second aperture capable of receiving a length of dental floss and for allowing the selected length of floss to pass therethrough. This aperture is positioned essentially at the free end of the finger portion. The first and second apertures extend essentially orthogonally to the longitudinal axis of the portion of the stick member through which it passes.

Normally, in use, the user may thread the selected length of floss through one of the first or second apertures into the other of the first or second apertures, so that a portion of the floss extends along one side of the finger portion between the apertures and a desired length of the floss terminating in a free end extends from the second aperture for manipulation by a first hand of the user. Alternatively, after the selected length of floss has been threaded through one of the first or second apertures, the user can wrap the floss around the finger portion a desired number of revolutions (i.e., a half revolution, a full revolution, one and a half revolutions, two revolutions, etc.) prior to threading the floss through the other of the first or second apertures. Accordingly, the side of the stick member through which the floss enters the first or second aperture may be either the same or the other side of the stick member through which the floss enters the other of the first or second aperture. The number of revolutions is selected to increase the friction between the floss and the stick member to aid in use without interfering with the free displacement of the floss relative to the stick member when desired to advance a fresh portion of the length of floss to the flossing position.

The user can fix the position of the selected length of floss relative to the stick member by exerting pressure on a portion of the floss against the stick member by the second hand. The user can hold the stick member by the handle portion so as to permit a digit(s) of the second hand to press the floss against the handle portion, the finger portion, or the entrance to the first aperture. The end of the dental floss that exits the second aperture is held by either a plurality of fingers or by wrapping the dental floss repeatedly around a finger of the user's first hand, and by creating tension on the dental floss, the desired length of dental floss between the user's first hand and the stick member is thereby kept taut. The finger portion then penetrates into the user's mouth and by using a back and forth motion or an up and down motion, or the like, food particles or plaque will be more readily dislodged. When a fresh length of floss is needed, all that is required is to release the pressure on the floss at or near the first aperture, pull the desired length of floss by using the first hand and reapplying pressure on the floss at or near the first aperture by a digit(s) of the user's second hand.

In an alternative embodiment, the finger and handle portions of the stick member are at an obtuse angle to each other. In still another embodiment only a single aperture is provided at the free end of the finger portion extending orthogonally to the longitudinal axis of the finger portion.

Accordingly, it is an object of the present invention to provide an improved dental flossing device and method.

Another object of the present invention is to provide an improved dental flossing device having a construction that will improve the reach of the dental floss into the user's mouth.

Another object of the present invention is to provide an improved dental flossing device and method having a construction that is easy to use and facilitates a user's transition from only using one's fingers to using the present invention.

Yet another object of the present invention is to provide an improved dental flossing method that facilitates individuals with diminished finger strength or coordination in using the improved dental flossing device, especially where the floss is particularly slippery.

Still another object of the present invention is to provide an improved dental flossing device having a construction that will help prevent gum disease by plaque removal, tooth decay, and gingivitis.

The invention accordingly comprises the several steps and the relation of one or more of such steps with respect to each of the others, and the apparatus embodying features of construction, combinations of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figures 1, 2:
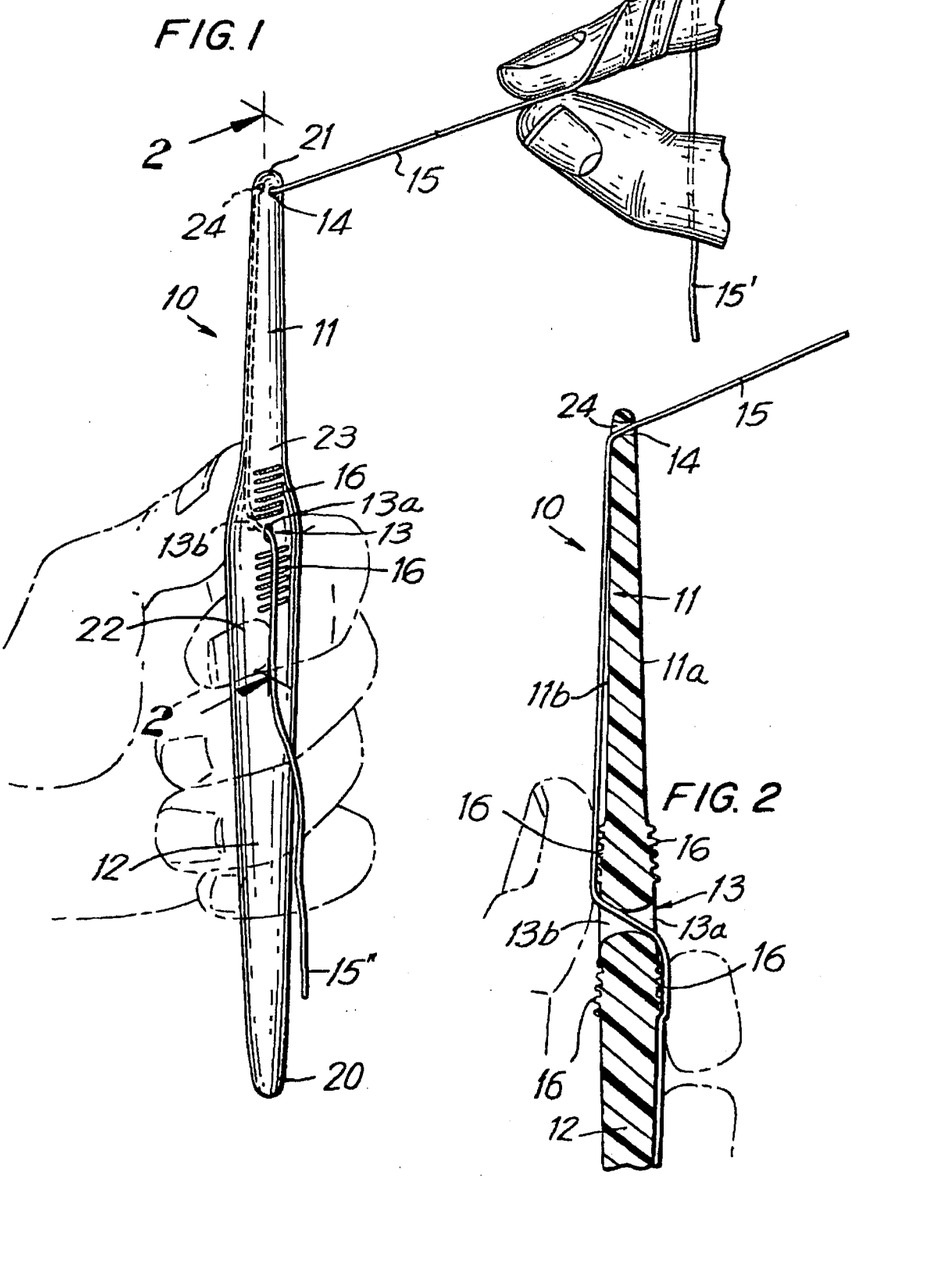
FIG. 1 is a perspective view of a dental flossing device in accordance with a first embodiment of the present invention.
FIG. 2 is a fragmentary cross-sectional view taken along line 2—2 of FIG. 1.

Reference is made to FIGS. 1 and 2 which illustrate a first embodiment of the apparatus for dental flossing of the present invention.

A dental flossing device for flossing, designated generally at 10, has a handle portion 12 and a finger portion 11. Handle portion 12 has a first end 20 and a second end 22. Finger portion 11 has a free end 21 and a near end 23. Near end 23 of finger portion 11 is joined to second end 22 of handle portion 12. In a preferred embodiment, flossing device 10 is made from a molded plastic such as polyurethane but it is understood that the device according to the present invention could also be made from wood, rubber, metal or other suitable hard materials.

Handle portion 12 is tapered from second end 22 to first end 20 of flossing device 10. Finger portion 11 is also illustrated as sharply tapered adjacent its near end 23 and then more gradually tapered as one approaches free end 21. However, flossing device 10 can also be designed such that only handle portion 12 or finger portion 11 is tapered, or neither handle portion 12 or finger portion 11 is tapered, thereby giving flossing device 10 a more rectangular shape.

However, the tapering of the handle portion 12 allows for a more comfortable grip and the tapering of finger portion 11 allows for easier penetration inside of the mouth and manipulation within the mouth. A further advantage of providing a major portion of finger portion 11 extending to the free end with a smaller cross-sectional area than both the junction between the finger and handle portions and most of the length of the handle portion, is that it permits the finger portion to flex to relieve tension on the floss when pulled. The thinness of handle portion 12 is constrained by comfort concerns and the thinness of the finger portion 11 is constrained primarily by the diameter of a second aperture 14 at the free end 21 and the minimum strength requirements for the finger portion. The smaller the diameter of second aperture 14, the more difficult it is to thread the floss therethrough.

The cross-sectional shape of flossing device 10 can be round, elliptical, or of any convenient shape that preferably does not have sharp edges on which the user could cut his or her mouth.

A key feature of the present invention is the utilization of only two apertures, a first aperture 13 and second aperture 14. First aperture 13 is located essentially at the junction where handle portion 12 and finger portion 11 join. Second aperture 14 is located near free end 21 of finger portion 11. As depicted in FIGS. 1 and 2, first aperture 13 and second aperture 14 both extend essentially orthogonal to the longitudinal axis of the portion of flossing device 10 through which they pass. The openings of both apertures are rounded to provide a smooth surface for the flossing material to ride along, thereby avoiding abrasion of the flossing material when it is advanced. The apertures are dimensioned to receive flossing material with a clearance to permit easy threading.

Flossing device 10 may also include friction ribs 16 extending laterally at a position above and/or below the openings 13a and 13b of first aperture 13. They may be provided on either handle portion 12, finger portion 11, or both and on one or both sides of either the handle or finger portions. Therefore, there can be up to four sets of friction ribs 16 on flossing device 10. In place of ribs, laterally extending friction grooves may be provided at one or more locations. Friction ribs 16 aid the user to fix the flossing material 15 by preventing flossing material 15 from sliding relative to handle portion 12 or finger portion 11 due to the frictional engagement between friction ribs 16 and the user's digit, such as a thumb. They can also prevent a digit from sliding along an otherwise smooth surface of the flossing device.

In addition, in place of ribs or grooves, pads may be used to aid the user in preventing the flossing material from sliding relative to handle portion 12 or finger portion 11. The pads may be molded in the handle portion and/or finger portion or may be adhered to the stick member with an adhesive. It is also to be understood that pads 16 could be used in combination with the friction ribs and/or friction grooves. Moreover, pads 16 may be made from material which is the same as the material that stick member 10 is made from or may be different material.

Figures 3, 4:
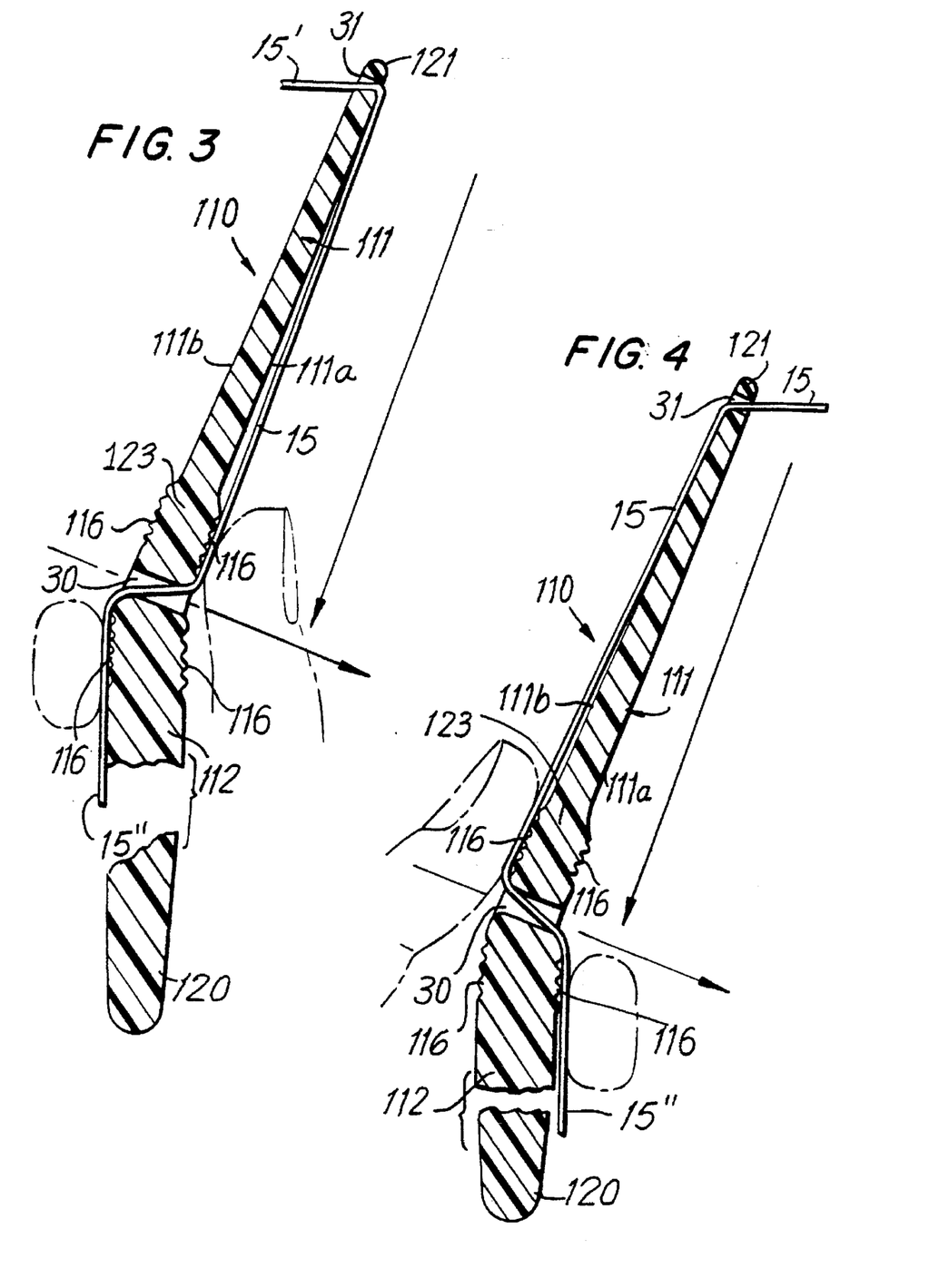
FIG. 3 is a fragmentary cross-sectional view in accordance with a second embodiment of the present invention.
FIG. 4 is a fragmentary cross-sectional view in accordance with the second embodiment of the present invention showing an alternative method of using the flossing device.

In the first embodiment of FIGS. 1 and 2, the flossing device 10 is essentially straight. As shown in FIGS. 3 and 4, in accordance with a second embodiment of the present invention, flossing device 110 is provided with a finger portion 111 which forms an obtuse angle with handle portion 112. Furthermore, a first aperture 30 and second aperture 31 are both located on finger portion 111, the first aperture being adjacent the near end 123 of finger portion 111, the second aperture being near the free end 121 of the finger portion. Both apertures extend orthogonal to the longitudinal axis of finger portion 111 through which they pass. This construction also allows for easy manipulation of finger portion 111 within the mouth of the user because of the angled relation between the handle and finger portions. It is also to be understood that an alternate embodiment can be constructed such that first aperture 30 is located on handle portion 112 with the aperture extending orthogonal to the longitudinal axis of finger portion 112. Friction ribs, grooves or pads 116 operate the same as friction ribs, grooves or pads 16. Similarly, pads 116 may be made from the same material as flossing device 110 or may be made from different material.

Features in FIGS. 3 and 4 similar in structure and operation to features in FIGS. 1 and 2 are assigned like reference numerals and described.

The finger portion of the embodiments of FIGS. 1–4 is preferably of a length from about one inch to about four inches from the junction of the finger and handle portions. If the finger portion is too short, the user's hand that holds the device must enter the mouth. If the finger portion is too long, it is difficult to control the free end and the device. The entire device is preferably of a length similar to that of conventional toothbrushes, so as to fit in conventional toothbrush cases.

The flossing devices in accordance with the invention of FIGS. 1–4 are preferably free of apertures therethrough intended for receiving the floss material aside from the first and second apertures. Thus, a hole at end 20 of flossing device 10 or at end 120 of flossing device 110 might be provided for mounting the device on a hook, but not to receive the floss. The flossing device in accordance with the invention is also preferably free of means for fixing the position of the floss other than by engagement of the floss against the flossing device by the user's hand or digits.

Figure 6:
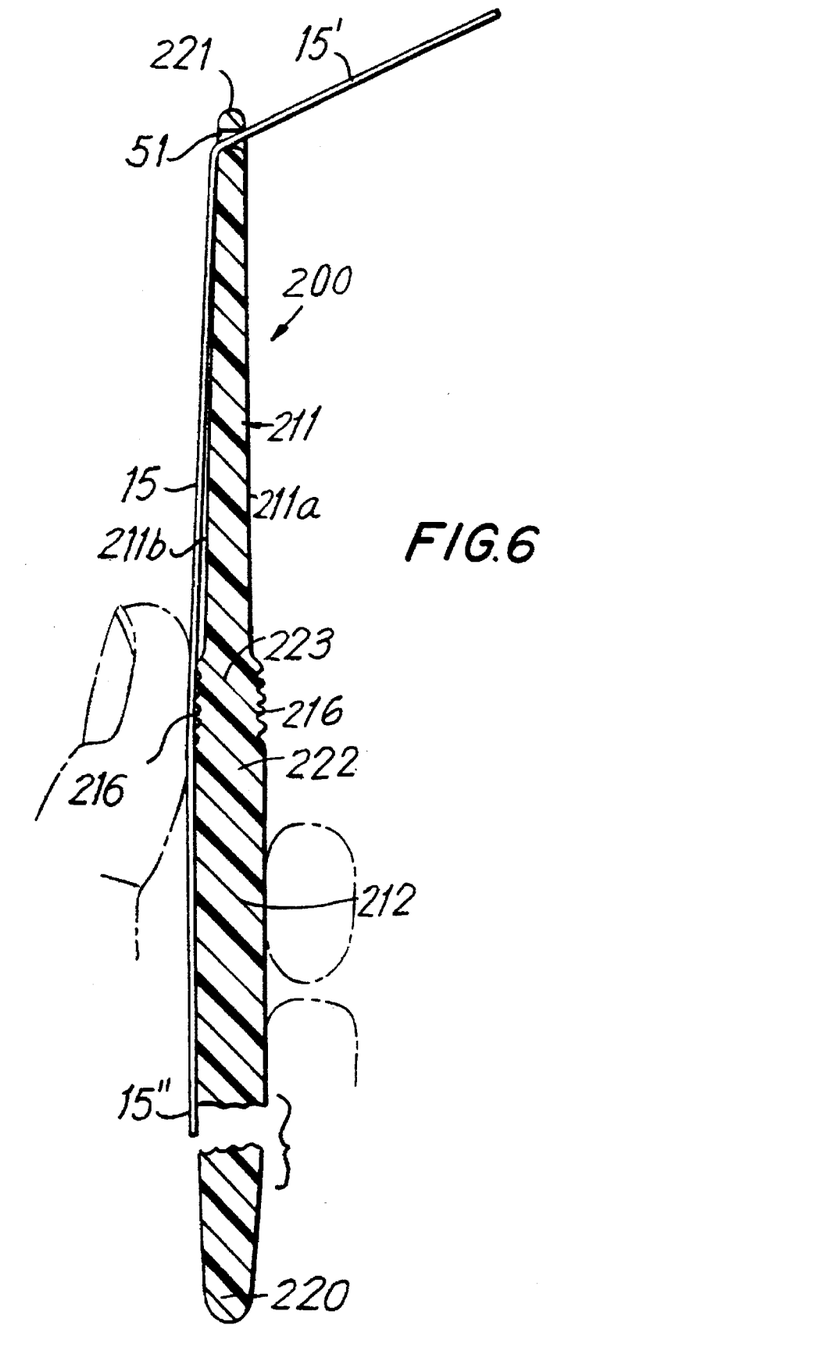
FIG. 6 is a cross-sectional view of a dental flossing device in accordance with a third embodiment of the present invention.

Reference is now made to FIG. 6 which illustrates a third embodiment of the present invention. The dental flossing device, designated generally at 200, has a handle portion 212 and a finger portion 211. Handle portion 212 has a first end 220 and a second end 222. Finger portion 211 has a free end 221 and a near end 223. Near end 223 of finger portion 211 is joined to second end 222 of handle portion 212.

In this third embodiment, there is only one aperture 51 located near free end 221 of finger portion 211. As depicted in FIG. 6, aperture 51 extends essentially orthogonal to the longitudinal axis of finger portion 211. Furthermore, features in FIG. 6, such as the tapering of finger portion 211 and/or handle portion 212, the material flossing device 200 is made from, the cross-sectional shape of flossing device 200, and the dimensions of the finger portion and of the device are similar in structure and operation to corresponding features in FIGS. 1 and 2 and are not repeated herein but it is understood that these features are applicable to the embodiment of FIG. 6. Also, handle portion 212 and finger portion 211 may form an obtuse angle with respect to each other similar to the angle formed by finger portion 111 and handle portion 112 depicted in FIGS. 3 and 4.

Flossing device 200 may also include friction ribs, grooves or pads 216 extending laterally on either handle portion 212, finger portion 211, or both, and on one or both sides of either the handle or finger portions. It is also understood that there may be one set of friction ribs 216 on either side of the flossing device extending from at least a portion of finger portion 211 to handle portion 212. Ribs, grooves or pads 216 operate in a similar manner to ribs, grooves or pads 16 and 116 and may be made from material different from or the same as that used to mold flossing device 200. The device 200 is otherwise free of means to which the floss can be secured to prevent movement relative to the device without being held by the hand of the user.

As in the case of the embodiments of FIGS. 1–4, a hole at first end 220 can be provided for mounting the device on a hook, but not to receive the floss. Also, as in the case of the embodiment of FIGS. 3 and 4, the longitudinal axis of the finger portion 211 of the embodiment of FIG. 6 can be formed at an obtuse angle to the longitudinal axis of the handle portion 212.

A description of one method of using the device of the present invention will now be provided with reference to FIGS. 1–2, the embodiment of FIGS. 3 and 4 operating in a like manner.

A selected length of flossing material 15 is introduced through entrance opening 13a of first aperture 13. Thereafter, flossing material 15 is led up the finger portion and passed through an entrance opening 24 of second aperture 14. The user holds flossing device 10 in a second hand with a digit(s) over first aperture 13, or a set of friction ribs 16 located above first aperture 13, and/or a set of friction ribs 16 over which the flossing material 15 passes as it extends down handle portion 12. Being mindful of not allowing all of flossing material 15 to pass through first aperture 13, the user holds the flossing material near a free end 15' thereof and slowly pulls on flossing material 15 so that there is a sufficient length of flossing material to effect flossing in accordance with one's personal technique of flossing. A sufficient amount of flossing material 15 adjacent free end 15' is needed to be able to grip with a plurality of fingers or to be able to wrap around one finger. The other free end 15" of flossing material 15 is thereafter pressed against handle portion 12 and/or finger portion 11 by the use of the user's digits in order to aid in the restraining of all of flossing material 15 from passing through first aperture 13. The pressure applied by the user's digit(s) to aperture 13 and/or friction ribs 16 should be sufficient to resist movement of the flossing material when held taut during use. The level of pressure required is minimized by taking advantage of the holding force applied to the flossing material as it passes or after it passes through first aperture 13.

It is also to be understood that threading flossing material 15 through first aperture 13 and second aperture 14 can also be accomplished by first threading flossing material 15 through second aperture 14 and thereafter threading flossing material 15 through first aperture 13.

Figure 5:
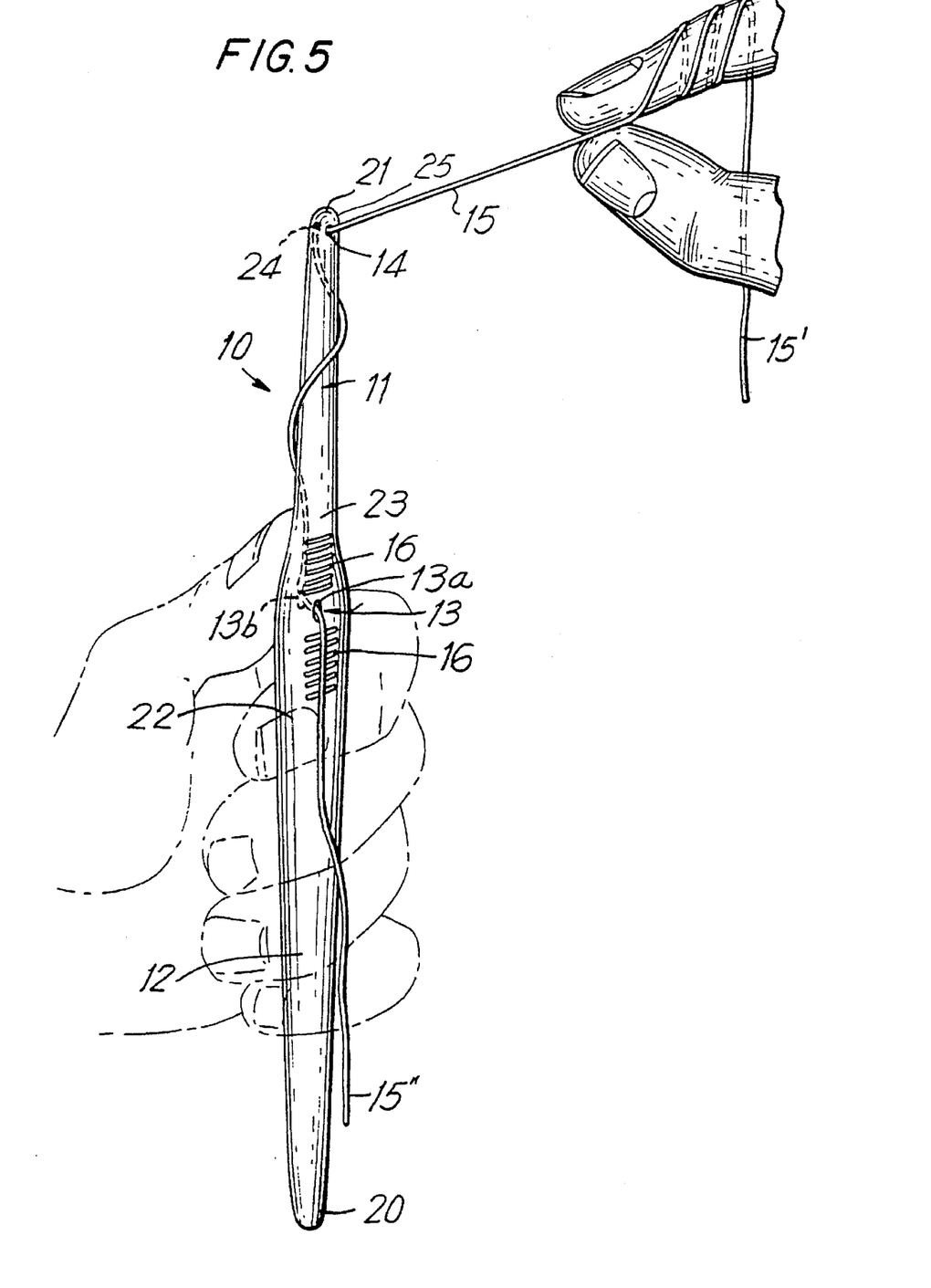
FIG. 5 is a perspective view of the dental flossing device depicted in FIG. 1 and illustrating an alternative method of threading a selected length of floss through the first and second apertures.

It is also contemplated that various types of flossing material may be used. For example, the floss may be waxed or unwaxed. It has been found that certain high-tech flosses provide less friction against the stick member and against one's skin than unwaxed floss. Furthermore, it has been found that individuals, such as the elderly, may have diminished finger strength or coordination which inhibits their ability to grasp the flossing material. Accordingly, an alternative method of flossing is provided which provides additional friction between the flossing material and the stick member without interfering with the function and operation of the stick member in accordance with the invention. Reference is now made to the device depicted in FIGS. 1 and 2, and the method of use to be explained with reference to FIG. 5. However, it is to be understood that the method of use to be explained in reference to FIG. 5 is also applicable to the embodiments of FIGS. 3 and 4.

Specifically, and similar to the aforementioned method, a selected length of flossing material 15 may be introduced through entrance opening 13a of first aperture 13. However, as flossing material 15 is led up finger portion 11, the user may wrap flossing material 15 around finger portion 11 one full revolution (by way of example) so that flossing material 15 may still be passed through entrance opening 24 of second aperture 14. In like manner, it is to be understood that threading flossing material 15 through first aperture 13 and second aperture 14 can also be accomplished by first threading flossing material 15 through an entrance opening 25 of second aperture 14, then wrapping flossing material 15 one full revolution around finger portion 11, and thereafter threading flossing material 15 through opening 13b of first aperture 13, so that flossing material 15 can exit opening 13a thereby ultimately achieving the same flossing configuration.

As noted, the wrapping of flossing material 15 only one full revolution around finger portion 11 is by way of example. It is contemplated that one may desire wrapping flossing material more or less than one revolution, such as one-half revolution, one and one-half revolutions, or two or more full revolutions around finger portion 11. If the user wraps flossing material 15 around finger portion 11 a non-integer number of revolutions, it is understood that the side of aperture 13 through which flossing material 15 enters will be the same side as the side of aperture 14 through which the flossing material enters.

The wrapping of the flossing material around the finger portion increases the friction of the floss against the stick member and assists an individual with diminished finger strength or control in using the flossing devices disclosed herein. The number of full or half revolutions that flossing material 15 is wrapped around finger portion 11 depends on the nature of the floss, the friction between the floss and the stick member and the strength and coordination of the user by determining the ease with which the user can hold the floss against the stick member and pull flossing material 15 so that there is a sufficient length of new floss to effect flossing when desired. However, it is important that the number of revolutions that flossing material 15 is wrapped around finger portion 11 cannot be so high that the friction force between the floss and the stick member is too great and prevents the free displacement of the floss through apertures 13 and 24 and around finger portion 11 when pressure on the floss against the stick member is relieved and the end 15' of floss 15 is pulled to present a fresh section of floss for use in flossing. Therefore, this aspect of the user's preferred flossing method and capabilities must be considered during the preparation of flossing.

Thereafter, the only necessary remaining step is to place free end 21 of flossing device 10 into the mouth and in accordance with the user's personal preference, move back and forth or up and down, using the present invention in conjunction with the user's fingers of the first hand holding flossing material 15. When an additional length of flossing material is needed, the user merely lessens the pressure of the digit(s) of his or her second hand and pulls the desired additional length with his or her first hand, using the digit pressure to closely control the amount of additional flossing material. The user then reapplies the digit pressure with the second hand, grabs the flossing material with his or her first hand nearer to flossing device 10 and proceeds with flossing.

It is further to be understood that the same methods of using the flossing device can be employed in accordance with the second embodiment depicted in FIGS. 3 and 4. In FIGS. 3 and 4, flossing material 15 is either threaded through first aperture 30 and thereafter threaded back through second aperture 31, or flossing material 15 can be first threaded through second aperture 31 and thereafter threaded through first aperture 30. As seen in FIGS. 3 and 4, flossing material 15 can be threaded through first and second apertures 30 and 31 so as to run along either one side 111a or the other side 111b of the finger portion.

Similarly, the various methods of wrapping flossing material 15 around finger portion 11, as discussed above, with particular reference to FIGS. 1, 2 and 5, is equally applicable to the embodiment of FIGS. 3 and 4.

A description of the method of using the device in accordance with the third embodiment will now be provided with reference to FIG. 6. A selected length of flossing material 15 is introduced through an entrance opening of aperture 51. Thereafter, flossing material 15 is led down a side of the finger portion where free end 15" of flossing material 15 is thereafter pressed against handle portion 212 and/or finger portion 211 by the use of a user's digit of one hand, such as a thumb, in order to restrain all of the flossing material 15 from passing through aperture 51. The pressure applied by the user's digit to free end 15" of flossing material 15 should be sufficient to resist movement of the flossing material when held taut during use. Furthermore, free end 15' of flossing material 15 is provided to effect flossing in accordance with one's personal technique of flossing, keeping in mind that a sufficient amount is needed to be able to grip with a plurality of fingers on the user's other hand or to be able to wrap around one finger of the user's other hand.

Flossing material 15 can be threaded through aperture 51 so as to run along either one side 211a or the other side 211b of finger portion 211 or flossing material 15 can be threaded through aperture 51 and thereafter, wrapped around finger portion 211 a half revolution, a full revolution, or a plurality or combination of either or both. Similar to the embodiments discussed above with respect to FIGS. 1–4 and 6, wrapping the floss around the stick member prior to the grasping thereof permits the use of a slippery type of floss and a user with diminished finger strength or coordination to enjoy the advantages of the invention disclosed herein. However, it is important that the number of revolutions that flossing material 15 is wrapped around the stick member cannot be so high that the friction force between the floss and the stick member is too great and prevents the free displacement of the floss through aperture 51 and around finger portion 211 when pressure on the floss against the stick member is relieved and end 15' of floss 15 is pulled to present a fresh section of floss for use in flossing.

Lastly, it is also to be understood that the embodiment of FIGS. 3 and 4 can be modified to comprise a handle portion and a finger portion having only one aperture 31 near free end 121 of finger portion 111.

The method of using the flossing device in accordance with this fourth embodiment would be similar to the method of using the flossing device as illustrated in FIGS. 3 and 4, except to the extent that free end 15" of flossing material 15 is pressed against either handle portion 112 and/or finger portion 111 by the use of the user's digit, such as a thumb on the hand holding the stick member, keeping in mind that the wrapping of the floss around the finger portion will assist in preventing the floss from being pulled through aperture 51 during use.

It will thus be seen that the objects set forth above, among those made apparent from the preceding description, are efficiently attained and, since certain changes may be made in the above constructions without departing from the spirit and scope of the invention, it is intended that all matter contained in the above description shall be interpreted as illustrative and not in a limiting sense.

By the device and method in accordance with the invention, an improved flossing tool is provided which is easy to use and easy to carry and store, while permitting effective flossing.

It is also to be understood that the following claims are intended to cover all of the generic and specific features of the invention herein described and all statements of the scope of the invention which, as a matter of language, might be said to fall therebetween.

What is claimed is:

1. A device for flossing teeth, comprising:

a length of floss having first and second ends;

an elongated stick member having a handle portion and a finger portion;

said handle portion having a first end and a second end;

said finger portion having a near end and a free end, said near end of said finger portion being connected to said second end of said handle portion, said stick member having a first side and a second side opposite said first side, said sides being intermediate said first end of said handle portion and said free end of said finger portion;

said stick member having a first aperture dimensioned to receive said floss, essentially positioned near the connection of said near end of said finger portion and said second end of said handle portion, said first aperture extending from said first side of said stick member to said second side of said stick member and essentially orthogonal to the longitudinal axis of the portion of said stick member through which it passes;

said finger portion having a second aperture positioned adjacent said free end of said finger portion dimensioned to receive said floss, said second aperture extending essentially orthogonal to the longitudinal axis of said finger portion from said first side of said stick member to said second side of said stick member, said length of floss being freely displaceable through said first and second apertures except when said floss is engaged against said stick member by the hand of the user holding the handle member, said length of floss extending from its first end through said second aperture from said first to said second side of said stick member and through said first aperture from one of said first and said second sides of said stick member to the other of said first and second sides of said stick member to the second end of said length of floss, the portion of said length of floss between said second aperture and said first end of said length of floss being free of connection to said stick member to permit said length of floss to be pulled from said first side of said stick member from said second aperture.

2. The device for flossing teeth, as claimed in claim 1, wherein said floss is wrapped around the finger portion at least one-half turn before entering said second aperture to increase the friction between said stick member and floss so that the pressure engaging the floss against the stick member can be reduced to prevent displacement of the floss relative to the stick member during flossing while not interfering with the free displacement of the floss through the first and second apertures during pulling of said floss through said first and second apertures when said pressure is relieved.

3. The device for flossing teeth, as claimed in claim 2, wherein said length of floss extends from its first end to its second end through said second aperture from said first to said second side of said stick member, along said first side of said finger portion of said stick member while being wrapped around said finger portion a number of turns selected from the group consisting of one-half and an integer plus one half and through said first aperture from said first to said second side of said stick member.

4. The device for flossing teeth, as claimed in claim 1, wherein said length of floss extends from its first end to its second end through said second aperture from said first to said second side of said stick member, along said second side of said finger portion of said stick member while being wrapped around said finger portion an integer number of rotations and through said first aperture from said second side to said first side of said stick member.

5. The device for flossing teeth, as claimed in claim 1, wherein said stick member includes friction means on at least one of said first and said second sides of said stick member for engagement of said floss by said hand of the user to prevent free displacement of said floss through said apertures.

6. The device for flossing teeth, as claimed in claim 5, wherein said friction means is positioned between said free end of said finger portion and said first aperture, said friction means comprising a plurality of laterally extending ribs.

7. The device for flossing teeth, as claimed in claim 5, wherein said friction means is provided on opposed sides of said first aperture as viewed along the length of said stick member.

8. The device for flossing teeth, as claimed in claim 1, wherein said handle portion is essentially tapered from its second to its first end.

9. The device for flossing teeth, as claimed in claim 1, wherein said finger portion is thinner in cross-sectional area at least in the region thereof extending from said free end thereof than the region of said stick member adjacent the near end of said finger portion.

10. The device for flossing teeth, as claimed in claim 9, wherein said finger portion is sufficiently flexible to permit said finger portion to flex at least a small distance in response to said floss being pulled from said first side of said stick member from said second aperture while said stick member is held by a user by said handle portion and a region of said floss is held against said stick member by the user to prevent relative displacement of the floss relative to the stick member.

11. The device for flossing teeth, as claimed in claim 1, wherein said finger portion is sufficiently flexible to permit said finger portion to flex at least a small distance in response to said floss being pulled from said first side of said stick member from said second aperture while said stick member is held by a user by said handle portion and a region of said floss is held against said stick member by the user to prevent relative displacement of the floss relative to the stick member.

12. The device for flossing teeth, as claimed in claim 1, wherein said stick member is formed from a material selected from the group consisting of plastic, wood, metal and rubber.

13. The device for flossing teeth, as claimed in claim 1, wherein said stick member is free of apertures therethrough intended for receipt of floss therethrough except for said first and second apertures.

14. The device for flossing teeth, as claimed in claim 1, wherein each of said first and second apertures have ends which are rounded in the direction of the length of the apertures toward adjacent surfaces of said finger portion.

15. The device for flossing teeth, as claimed in claim 1, wherein said finger portion is of a length from about one inch to about four inches.

16. The device for flossing teeth, as claimed in claim 1, wherein said handle portion has a longitudinal axis and said finger portion has a longitudinal axis, said longitudinal axis of said handle portion and said longitudinal axis of said finger portion forming an obtuse angle.

17. A device for flossing teeth, comprising:

a length of floss having first and second ends;

an elongated stick member having a handle portion and a finger portion;

said handle portion having a first end and a second end;

said finger portion having a near end and a free end, said near end of said finger portion being connected to said second end of said handle portion, said stick member having a first side and a second side opposite said first side, said sides being intermediate said first end of said handle portion and said free end of said finger portion;

said finger portion having a single aperture positioned essentially adjacent said free end of said finger portion dimensioned to receive said length of floss, said aperture extending from said first side of said stick member to said second side of said stick member and essentially orthogonal to the longitudinal axis of said finger portion, said length of floss being freely displaceable through said aperture, said length of floss extending from its first end through said aperture from a first to a second side of said stick member and along at least a portion of said stick member to at least about the near end of said finger portion to permit said floss to be pulled from said first side of said stick member, said stick member including a region on a side thereof against which said floss can be pressed by the hand of a user holding said handle portion, said stick member being otherwise free of apertures therethrough designed to receive floss and free of means to which said floss can be secured to prevent movement relative to said stick member without being held by the hand of the user.

18. The device for flossing teeth, as claimed in claim 17, wherein said floss is wrapped around said finger portion at least one-half turn after passing through said single aperture to increase the friction between the floss and the stick member so that pressure engaging the floss against the stick member can be reduced to prevent displacement of said floss relative to said stick member during flossing while not interfering with the free displacement of the floss through the single aperture during pulling of the floss from the first side of the stick member from said single aperture when said pressure is relieved.

19. The device for flossing teeth, as claimed in claim 17, wherein said stick member includes friction means on at least said second side of said stick member for engagement of said floss by the hand of the user to prevent free displacement of said floss through said aperture.

20. The device for flossing teeth, as claimed in claim 19, wherein said stick member includes said friction means on both said first and second sides of said stick member.

21. The device for flossing teeth, as claimed in claim 17, wherein said finger portion is sufficiently flexible to permit said finger portion to flex at least a small distance in response to said floss being pulled from said first side of said stick member from said aperture while said stick member is held by a user by said handle portion and a region of said floss is held against said stick member by the user to prevent relative displacement of the floss relative to the stick member.

22. The device for flossing teeth, as claimed in claim 17, wherein said stick member is formed from a material selected from a material selected from the group consisting of plastic, wood, metal and rubber.

23. The device for flossing teeth, as claimed in claim 17, wherein said finger portion is thinner in cross-sectional area at least in the region thereof extending from said free end thereof than the region of said stick member adjacent the near end of said finger portion.

24. The device for flossing teeth, as claimed in claim 17, wherein said handle portion has a longitudinal axis and said finger portion has a longitudinal axis, said longitudinal axis of said handle portion and said longitudinal axis of said finger portion forming an obtuse angle.

25. A method for flossing teeth comprising:

providing an elongated stick member having a handle portion and a finger portion, said handle portion having a first end and a second end, said finger portion having a near end and a free end, said near end of said finger portion being connected to said second end of said handle portion, said finger portion having a first aperture dimensioned to receive floss, essentially positioned near the connection of said near end of said finger portion and said second end of said handle portion, said first aperture extending essentially orthogonal to the longitudinal axis of said stick member, said finger portion having a second aperture positioned essentially at said free end of said finger portion dimensioned to receive floss, said second aperture extending essentially orthogonal to the longitudinal axis of said finger portion;

threading a length of floss through one of said first and second apertures from a first to a second side of said stick member, wrapping said floss at least one half turn around the finger portion and then threading said length of floss through said other of said first and second apertures from one of said first and said second sides of said stick member to the other of said first and said second sides of said stick member;

providing a sufficient length of floss extending from said second aperture to permit grasping by a first hand of a user at a position spaced from said second aperture while said handle portion is held in a second hand of the user;

clamping by the second hand of the user at least one of the portion of said floss between said first aperture and said second aperture and the portion of said floss extending from said first aperture, against a side of said stick member; and performing flossing by inserting the free end of said finger portion into the mouth of the user and moving the portion of said floss between said first hand and said second aperture by manipulation of said first and second hands.

26. The method of claim 25, wherein said clamping step is performed by a digit of said second hand of said user.

27. The method of claim 25, including wrapping a portion of said length of floss around at least a portion of said finger portion an integer number of turns after said length of floss is threaded through one of said first and second apertures from a first to a second side and before the length of floss is threaded through said other of said first and second apertures from said second side to said first side of said stick member.

28. The method of claim 25, including wrapping a portion of said length of floss around at least a portion of said finger portion a number of turns selected from the group including one-half and an integer plus one half after said length of floss is threaded through one of said first and second apertures from a first to a second side and before the length of floss is threaded through said other of said first and second apertures from said first side to said second side of said stick member.

29. The method of claim 25, and including the further step of releasing the clamping of said floss by the second hand of said user, pulling an additional length of floss through the second aperture by the first hand of the user, grasping said pulled floss at a position spaced from said second aperture and reclamping the portion of said floss extending from said first aperture against said stick member, the number of turns of said wrapping being selected to permit free displacement of said floss relative to said stick member when the clamping of said floss against said stick member is relieved.

30. A method for flossing teeth comprising:

providing an elongated stick member having a handle portion and a finger portion, said handle portion having a first end and a second end, said finger portion having a near end and a free end, said near end of said finger portion being connected to said second end of said handle portion, said stick member having a first side and a second side opposite said first side, said sides being intermediate said first end of said handle portion and said free end of said finger portion;

said finger portion having an aperture positioned essentially at said free end of said finger portion dimensioned to receive floss, said aperture extending essentially orthogonal to the longitudinal axis of said finger portion from said first side of said stick member to said second side of said stick member;

threading a length of floss through said aperture between said first and said second sides of said stick member;

providing a sufficient length of floss extending from said aperture at said first side of said stick member to permit grasping by a first hand of a user at a position spaced from said aperture while said handle portion is held in a second hand of the user;

providing a sufficient further length of floss extending from said aperture at said second side of said stick member to permit manual clamping of said length of floss against said stick member;

wrapping a portion of said further length of floss at least one half turn around the finger portion;

clamping by the second hand of the user a portion of said further length of floss extending from said wrapped portion against said stick member, leaving said floss otherwise free of connection to said stick member; and performing flossing by inserting the free end of said stick member into the mouth of the user and moving the portion of said floss between said first hand and said aperture by manipulation of said first and second hands.

31. The method of claim 30, including wrapping a portion of said further length of floss around said finger portion an integer number of turns between said aperture and the point of clamping to the stick member to increase the friction between the floss and the stick member so that pressure engaging the floss against the stick member can be reduced to prevent displacement of said floss relative to said stick member during flossing while not interfering with the free displacement of the floss through the aperture during pulling of the floss from the first side of the stick member from said single aperture when said pressure is relieved.

32. The method of claim 30, including wrapping a portion of said further length of floss around said finger portion a number of turns selected from the group including one-half and an integer plus one half between said aperture and the point of clamping to the stick member to increase the friction between the floss and the stick member so that pressure engaging the floss against the stick member can be reduced to prevent displacement of said floss relative to said stick member during flossing while not interfering with the free displacement of the floss through the aperture during pulling of the floss from the first side of the stick member from said single aperture when said pressure is relieved.

33. The method of claim 30, wherein said clamping step is performed by a digit of said second hand of said user.

34. The method of claim 30, and including the further step of releasing the clamping of said floss by the second hand of said user, pulling an additional length of floss through said aperture by the first hand of the user, grasping said pulled floss at a position spaced from said aperture and manually reclamping the further length of floss extending from said wrapped portion against said stick member.

* * * * *